United States Patent [19]

Tomesch et al.

[11] Patent Number: 4,868,319

[45] Date of Patent: Sep. 19, 1989

[54] PROCESS FOR THE PREPARATION OF MONOALKYLCARBAMATE GROUP-CONTAINING COMPOUNDS

[75] Inventors: John C. Tomesch, Succasunna; Mahavir Prashad, Hopatcong; William J. Houlihan, Mountain Lakes, all of N.J.

[73] Assignee: Sandoz Pharm. Corp., E. Hanover, N.J.

[21] Appl. No.: 136,893

[22] Filed: Dec. 22, 1987

[51] Int. Cl.$^4$ ............................................. C07D 307/16
[52] U.S. Cl. ....................................... 549/496; 560/32; 560/33; 560/163; 560/166
[58] Field of Search .................... 549/496; 560/32, 33, 560/163, 166

[56] References Cited

U.S. PATENT DOCUMENTS

| 4,582,824 | 4/1986 | Nishikawa et al. | 514/77 |
| 4,619,917 | 10/1986 | Lee et al. | 514/77 |

FOREIGN PATENT DOCUMENTS 178261  4/1986  European Pat. Off. .

*Primary Examiner*—Richard L. Raymond
*Attorney, Agent, or Firm*—Gerald D. Sharkin; Robert S. Honor; Joseph J. Borovian

[57] ABSTRACT

An improved process for preparing monoalkylcarbamate group-containing compounds comprising reacting a hydroxy group-containing compound with an organic halide and an alkali metal cyanate in the conjoint presence of a phase transfer catalyst and a solvent.

52 Claims, No Drawings

PROCESS FOR THE PREPARATION OF MONOALKYLCARBAMATE GROUP-CONTAINING COMPOUNDS

The present invention relates to an improved process for preparing monoalkylcarbamate group-containing compounds comprising reacting a hydroxy group-containing compound with an organic halide and an alkali metal cyanate in the conjoint presence of a phase transfer catalyst and a solvent.

Suitable monoalkylcarbamate group-containing compounds which may be prepared by the process of the invention include the monocyclic compounds having the formula I:

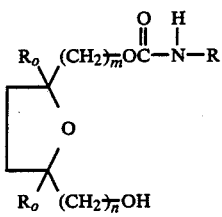

where
both $R_o$'s are the same and are either hydrogen or methyl;
R is n-$CH_{12}$–$C_{20}$ alkyl, alkenyl or alkynyl, $C_{12}$–$C_{24}$ alkoxyalkyl or $C_7$–$C_9$ phenylalkyl; and
m and n are, independently, an integer 1 or 2.

In the above formula, preferred compounds are those where both $R_o$'s are hydrogen or methyl, R is n-$C_{12}$–$C_{20}$ alkyl, and m and n are each 1. The more preferred compounds of the above formula are those where both $R_o$'s are hydrogen or methyl, R is n-$C_{14}$–$C_{20}$ alkyl, and m and n are each 1. The even more preferred compounds of the above formula are those where both $R_o$'s are hydrogen or methyl, R is n-$C_{16}$–$C_{20}$ alkyl, and m and n are each 1. The most preferred compounds of the above formula are cis-2-[(octadecylaminocarbonyl)oxy]methyl-5-hydroxymethyl tetrahydrofuran having the formula

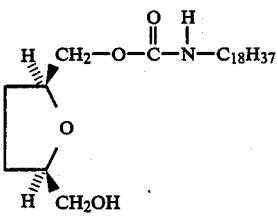

and cis-2-[(octadecylaminocarbonyl)oxy]methyl-5-hydroxymethyl-2,5-dimethyl tetrahydrofuran having the formula

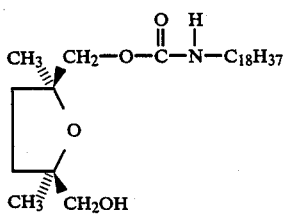

All of the above monocyclic compounds of formula I are known, having been previously described in European Pat. No. 178,261, issued on Apr. 16, 1986. Moreover, their usefulness as intermediates in the preparation of pharmacologically active compounds is set forth therein.

Other suitable monoalkylcarbamate group-containing compounds which may be prepared by the process of this invention are the monocyclic compounds having the formula II:

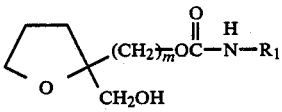

where
$R_1$ is n-$C_{12}$–$C_{20}$alkyl, alkenyl or alkynyl, or $C_{12}$–$C_{24}$alkoxyalkyl; and
m is an integer 1 or 2.

In the above formula, preferred compounds are those where $R_1$ is n-$C_{12}$–$C_{20}$alkyl and m is 1. The more preferred compounds of the above formula are those where $R_1$ is n-$C_{14}$–$C_{20}$ alkyl and m is 1. The even more preferred compounds of the above formula are those where $R_1$ is n-$C_{16}$–$C_{20}$alkyl and m is 1. The most preferred compound of the above formula is 2-hydroxymethyl-2-[(octadecylaminocarbonyl)oxy]methyl tetrahydrofuran having the formula

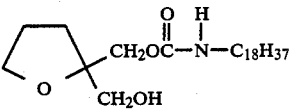

All of the above monocyclic compounds of formula II are known, having been described in U.S. Pat. No. 4,619,917, issued on Oct. 28, 1986. Moreover, their usefulness in the preparation of pharmacologically active compounds is set forth therein.

Still other suitable monoalkylcarbamate group-containing compounds which may be prepared by the process of this invention are the compounds of formula III:

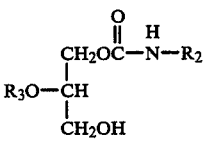

where
$R_2$ is $C_{10}$–$C_{24}$ alkyl; and
$R_3$ is $C_1$–$C_4$alkyl or $C_7$–$C_9$-phenylalkyl.

In the above formula, preferred compounds are those where $R_2$ is $C_{14}$–$C_{20}$ alkyl, and $R_3$ is $C_1$–$C_3$ alkyl or benzyl. The more preferred compounds of the above formula are those where $R_2$ is $C_{15}$–$C_{18}$ alkyl, and $R_3$ is methyl or benzyl. The even more preferred compounds of the above formula are those where $R_2$ is $C_{15}$–$C_{18}$ alkyl and $R_3$ is methyl. The most preferred compound of the above formula is 3-(N-octadecylcarbamoyloxy)-2-methoxy-1-propanol having the formula

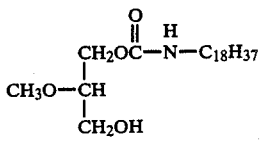

All of the above compounds of formula III are known, having been described in U.S. Pat. No. 4,582,824, issued on Apr. 15, 1986. Moreover, their usefulness in the preparation of pharmacologically active compounds is set forth therein.

In contrast to the processes described in European Pat. No. 178,261, U.S. Pat. No. 4,619,917 and U.S. Pat. No. 4,582,824, the process of the present invention utilizes inexpensive and readily available raw materials and results in higher yields of the monoalkylcarbamate group-containing compounds being produced.

In accordance with the process of the instant invention, the above-depicted monocyclic compounds of formula I or formula II, or the compounds of formula III, are prepared by reacting a monocyclic diol compound of formula I':

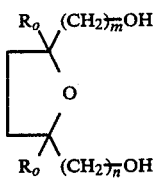 I' where the $R_o$'s, m and n are as defined above, a monocyclic diol compound of formula II':

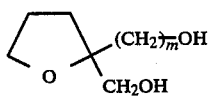 II' where m is as defined above, or a diol compound of formula III'

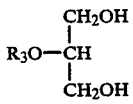 III' where $R_3$ is defined above, with an organic halide of formula IV:

 D—X  IV where D has the same significances as that defined above for R, $R_1$ or $R_2$ and X is halide, and an alkali metal cyanate of formula V:

 M—OCN  V where M is an alkali metal, in the conjoint presence of a phase transfer catalyst and a solvent to produce the desired monocyclic compounds of formula I or formula II, or the compounds of formula III, respectively.

As to the organic halides of formula IV., the preferred, more preferred and even more preferred significances of D are as set forth above regarding R, $R_1$ and $R_2$, whereas X is preferably chloride or bromide, more preferably bromide.

Although any alkali metal cyanate of formula V may be employed in the process of the instant invention, preferred cyanates are sodium cyanate and potassium cyanate, more preferably potassium cyanate. In general, the alkali metal cyanate is employed in an amount which is more or less equimolar to the amount of the organic halide. Preferably, the alkali metal cyanate is employed in an amount which is in slight excess to the amount of the organic halide.

With regard to the phase transfer catalysts, preferred are tetrabutyl ammonium bromide, benzyl triethyl ammonium bromide, methyl triphenyl phosphonium bromide and the crown ethers, e.g., 18-crown-6, more preferably tetrabutyl ammonium bromide. The phase transfer catalyst is employed in an amount of from 0.05 to about 0.50 molar equivalents of the monocyclic diol compound of formula I' or II', or the diol compound of formula III', preferably in an amount of from 0.10 to about 0.20 molar equivalents of the monocyclic diol compound of formula I' or II', or the diol compound of formula III'.

Although the nature of the solvent employed in the instant process is not critical, preferred solvents include the lower alkyl ($C_1$-$C_3$)nitriles, e.g., acetonitrile, and aromatic hydrocarbons, e.g., benzene, toluene and the like. The, more preferred solvent for the use in the instant process is acetonitrile.

The preparation of the monocyclic compounds of formula I or formula II, or the compounds of formula III is conducted at a temperature of from 20° to 120° C., preferably 20° to 100° C., more preferably 25° to 100° C.

The monocyclic diol compounds of formula I' and II', and the diol compounds of formula III', are either known and obtained by methods described in the literature, or where not known, may be obtained by methods analogous to those described in the literature.

The following examples are for the purposes of illustration only and are not intended in any way to limit the scope of the instant invention.

EXAMPLE 1

Cis-2-[(octadecylaminocarbonyl)oxy]methyl-5-hydroxymethyl tetrahydrofuran

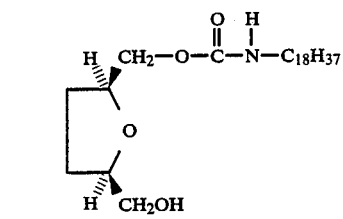

A suspension of 2.64 g (20 mmol) of cis-2,5-bis(hydroxymethyl)tetrahydrofuran, 7.99 g (24 mmol) of octadecyl bromide, 2.43 g (30 mmol) of potassium cyanate and 0.966 g (3 mmol) of tetrabutyl ammonium bromide in 100 ml of dry acetonitrile was refluxed, with stirring, at 100° C. for 20 hours. The resultant mixture was then diluted with hot methylene chloride, filtered and the filtrate concentrated in vacuo. The crude product was then purified by flash silica gel chromatography employing successive mixtures of petroleum ether and ethyl acetate in ratios of 4:1, 2.33:1 and 1:1 as the eluent to yield the title compound as a solid, m.p. 79°–80° C.

EXAMPLE 2

Cis-2-[(octadecylaminocarbonyl)oxy]methyl-5-hydroxymethyl-2,5-dimethyl tetrahydrofuran

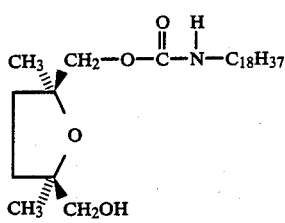

A suspension of 9.6 g (60 mmol) of cis-2,5-dimethyl-2,5-bis(hydroxymethyl)tetrahydrofuran, 24 g (72 mmol) of octadecyl bromide, 6 g (75 mmol) of potassium cyanate and 2.9 g (9 mmol) of tetrabutyl ammonium bromide in 300 ml of dry acetonitrile was refluxed, with stirring, at 100°C. for 17 hours. The resultant mixture was then diluted with hot methylene chloride, filtered and the filtrate concentrated in vacuo. The crude product was then purified by flash silica gel chromatography employing a mixture of petroleum ether and ethyl acetate in a 4:1 ratio as the eluent to yield the title compound as a solid, m.p. 45°–47° C.

EXAMPLE 3

Following essentially the procedure of Example 1, and using in place of the tetrabutyl ammonium bromide, an equivalent amount of benzyl triethyl ammonoium bromide, methyl triphenyl phosphonium bromide and 18-crown-6, respectively, the compound of Example 1 was obtained in approximately equivalent yields.

EXAMPLE 4

Following essentially the procedure of Example 2, and using in place of the octadecyl bromide, an equivalent amount of:
(a) pentadecyl bromide; and
(b) benzyl bromide;
there was obtained
(A) cis-2-[(pentadecylaminocarbonyl)oxy]methyl-5-hydroxymethyl-2,5-dimethyl tetrahydrofuran as an oil; and
(B) cis-2-[(benzylaminocarbonyl)oxy]methyl-5-hydroxymethyl-2,5-dimethyl tetrahydrofuran as an oil, respectively.

EXAMPLE 5

2-Hydroxymethyl-2-[(octadecylaminocarbonyl)oxy]methyl tetrahydrofuran

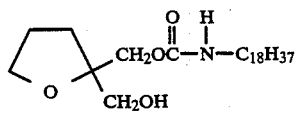

A suspension of 2.64 g (20 mmol) of 2,2-bis(hydroxymethyl)tetrahydrofuran, 7.99 g (24 mmol) of octadecyl bromide, 2.43 g (30 mmol) of potassium cyanate and 0.644 g (2 mmol) of tetrabutyl ammonium bromide in 300 ml of dry acetonitrile was refluxed, with stirring, at 100° C. for 23 hours. The resultant mixture was then diluted with hot methylene chloride, filtered and the filtrate concentrated in vacuo. The crude product was then purified by flash silica gel chromatography employing a mixture of petroleum ether and ethyl acetate in a 4:1 ratio as the eluent to yield the title compound as a solid, m.p. 57°–58° C.

EXAMPLE 6

3-(N-octadecylcarbamoyloxy)-2-methoxy-1-propanol

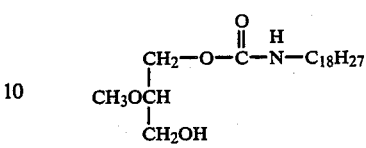

A suspension of 2.12 g (20 mmol) of 2-methoxy-1,3-propanediol 7.99 g (24 mmol) of octadecyl bromide, 2.43 g (30 mmol) of potassium cyanate and 1.29 g (4 mmol) of tetrabutyl ammonium bromide in 100 ml of dry acetonitrile was refluxed with stirring, at 100° C. for 24 hours. The resultant mixture was then diluted with hot methylene chloride, filtered and the filtrate concentrated in vacuo. The crude product was then purified by flash silica gel chromatography employing a mixture of petroleum ether and ethyl acetate in a 4:1 ratio as the eluent to yield the title compound as a solid, m.p. 56°–58° C.

What is claimed is:

1. A process for preparing a compound of formula I:

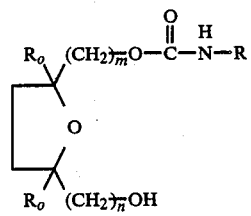

where
both $R_o$'s are the same and are either hydrogen or methyl;
R is n-$C_{12}$-$C_{20}$ alkyl, alkenyl or alkynyl, $C_{12}$-$C_{24}$-alkoxyalkyl or $C_7$-$C_9$-phenylalkyl; and
m an n are, independently, an integer 1 or 2,
which comprises reacting a monocyclic diol compound of formula I':

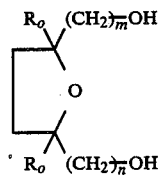

where
the $R_o$'s, m and n are as defined above,
with an organic halide of formula IV:

$$D-X \qquad \text{IV}$$

where
D has the same significances as that defined above for R; and
X is halide,
and an alkali metal cyanate of formula V:

M—OCN  V where
M is an alkali metal, in the conjoint presence of a phase transfer catalyst and a solvent at a temperature of from 20° to 120° C. to obtain said compound of formula I, the phase transfer catalyst being present in an amount of from 0.05 to about 0.50 molar equivalents of the monocyclic diol compound of formula I'.

2. A process according to claim 1 wherein the compound of formula I prepared is one where both $R_o$'s are hydrogen or methyl, R is n-$C_{12}$-$C_{20}$ alkyl, and m and n are 1.

3. A process according to claim 2 wherein the compound of formula I prepared is one where both $R_o$'s are hydrogen or methyl, R is n-$C_{14}$-$C_{20}$ alkyl, and m and n are 1.

4. A process according to claim 3 wherein the compound of formula I prepared is one where both $R_o$'s are hydrogen or methyl, R is n-$C_{16}$-$C_{20}$ alkyl, and m and n are 1.

5. A process according to claim 4 wherein the compound of formula I prepared has the formula

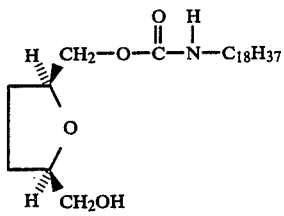

6. A process according to claim 4 wherein the compound of formula I prepared has the formula

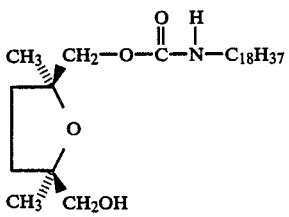

7. A process according to claim 1 wherein X in the compound of formula IV is chloride or bromide.

8. A process according to claim 7 wherein X in the compound of formula IV is bromide.

9. A process according to claim 1 wherein M in the compound of formula V is potassium or sodium.

10. A process according to claim 9 wherein M in the compound of formula V is potassium.

11. A process according to claim 1 wherein the phase transfer catalyst is selected from the group consisting of tetrabutyl ammonium bromide, benzyl triethyl ammonium bromide, methyl triphenyl phosphonium bromide and crown ethers.

12. A process according to claim 11 wherein the phase transfer catalyst is tetrabutyl ammonium bromide.

13. A process according to claim 1 wherein the phase transfer catalyst is present in an amount of from 0.10 to about 0.20 molar equivalents of the monocyclic diol compound of formula I'.

14. A process according to claim 1 wherein the solvent employed is a lower alkyl ($C_1$-$C_3$) nitrile.

15. A process according to claim 14 wherein the solvent employed is acetonitrile.

16. A process according to claim 1 wherein the temperature is from 20° to 100° C.

17. A process according to claim 16 wherein the temperature is from 25° to 100° C.

18. A process according to claim 1 for preparing a compound of formula I:

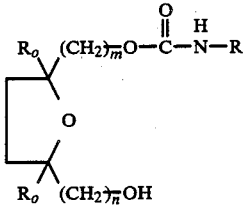

where
both $R_o$'s are the same and are hydrogen or methyl;
R is n-$C_{16}$-$C_{20}$ alkyl; and m and n are 1,
which comprises reacting a monocyclic diol compound of formula I':

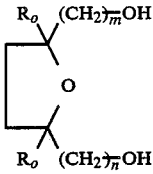

where
the $R_o$'s, m and n are as defined above,
with an organic halide of formula IV:

D—X  IV where
D has the same significance as R defined above; and
X is chloride or bromide, and
an alkali metal cyanate of formula V:

M—OCN  V where
M is potassium or sodium, in the conjoint presence of a phase transfer catalyst selected from the group consisting of tetrabutyl ammonium bromide, benzyl triethyl ammonium bromide, methyl triphenyl phosphonium bromide and 18-crown-6 and a lower alkyl ($C_1$-$C_3$) nitrile at a temperature of from 25° to 100° C. to obtain said compound of formula I, the phase transfer catalyst being present in an amount of from 0.10 to about 0.20 molar equivalents of the monocyclic diol compound of formula I'.

19. A process for preparing a compound of formula II:

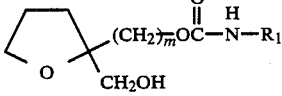

where
$R_1$ is n-$C_{12}$-$C_{20}$alkyl, alkenyl or alkynyl, or $C_{12}$-$C_{24}$alkoxyalkyl; and m is an integer 1 or 2,
which comprises reacting a monocyclic diol compound of formula II′:

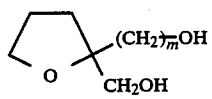    II′ where
m is as defined above,
with an organic halide of formula IV:

D—X    IV where
D has the same significances as that defined above for R₁; and
X is halide,
and an alkali metal cyanate of formula V:

M—OCN    V where
M is an alkali metal, in the conjoint presence of a phase transfer catalyst and a solvent at a temperature of from 20° to 120° C., to obtain said compound of formula II, the phase transfer catalyst being present in an amount of from 0.05 to about 0.50 molar equivalents of the monocyclic diol compound of formula II′.

20. A process according to claim 19 wherein the compound of formula II prepared is one where R₁ is n-C₁₂-C₂₀ alkyl and m is 1.

21. A process according to claim 20 wherein the compound of formula II prepared is one where R₁ is n-C₁₄-C₂₀alkyl and m is 1.

22. A process according to claim 21 wherein the compound of formula II prepared is one where R₁ is n-C₁₆-C₂₀ alkyl and m is 1.

23. A process according to claim 22 wherein the compound of formula II prepared has the formula

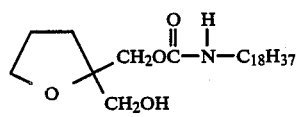

24. A process according to claim 19 wherein X in the compound of formula IV is chloride or bromide.

25. A process according to claim 24 wherein X in the compound of formula IV is bromide.

26. A process according to claim 19 wherein M in the compound of formula V is potassium or sodium.

27. A process according to claim 26 wherein M in the compound of formula V is potassium.

28. A process according to claim 19 wherein the phase transfer catalyst is selected from the group consisting of tetrabutyl ammonium bromide, benzyl triethyl ammonium bromide, methyl triphenyl phosphonium bromide and crown ethers.

29. A process according to claim 28 wherein the phase transfer catalyst is tetrabutyl ammonium bromide.

30. A process according to claim 19 wherein the phase transfer catalyst is present in an amount of from 0.10 to about 0.20 molar equivalents of the monocyclic diol compound of formula II′.

31. A process according to claim 19 wherein the solvent employed is a lower alkyl (C₁-C₃) nitrile.

32. A process according to claim 31 wherein the solvent employed is acetonitrile.

33. A process according to claim 19 wherein the temperature is from 20° to 100° C.

34. A process according to claim 33 wherein the temperature is from 25° to 100° C.

35. A process according to claim 20 for preparing a compound of formula II:

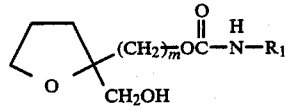    II where
R₁ is n-C₁₆-C₂₀alkyl; and
m is 1,
which comprises reacting a monocyclic diol compound of formula II′:

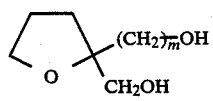    II′ where
m is as defined above,
with an organic halide of formula IV:

D—X    IV where
D has the same significance as R₁ defined above; and
X is chloride or bromide,
and an alkali metal cyanate of formula V:

M—OCN    V where
M is potassium or sodium, in the conjoint presence of a phase transfer catalyst selected from the group consisting of tetrabutyl ammonium bromide, benzyl triethyl ammonium bromide, methyl triphenyl phosphonium bromide and 18-crown-6 and a lower alkyl (C₁-C₃)nitrile at a temperature of from 25° to 100° C. to obtain said compound of formula II, the phase transfer catalyst being present in an amount of from 0.10 to about 0.20 molar equivalents of the monocyclic diol compound of formula II′.

36. A process for preparing a compound of formula III:

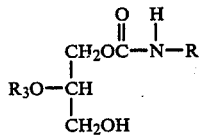    III where
R₂ is C₁₀-C₂₄ alkyl; and
R₃ is C₁-C₄ alkyl or C₇-C₉-phenylalkyl,
which comprises reacting a diol compound of formula III′:

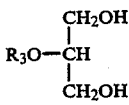

where
R$_3$ is as defined above,
with an organic halide of formula IV:

D—X                                                          IV where
D has the same significance as that defined above for R$_2$; and
X is halide,
and an alkali metal cyanate of formula V:

M—OCN                                                       V where
M is an alkali metal, in the conjoint presence of phase transfer catalyst and a solvent at a temperature of from 20° to 120° C. to obtain said compound of formula III, the phase transfer catalyst being present in an amount of from 0.05 to about 0.50 molar equivalents of the diol compound of formula III'.

37. A process according to claim 36 wherein the compound of formula III prepared is one where R$_2$ is C$_{14}$–C$_{20}$ alkyl, and R$_3$ is C$_1$–C$_3$ alkyl or benzyl.

38. A process according to claim 37 wherein the compound of formula III prepared is one where R$_2$ is C$_{15}$–C$_{18}$ alkyl, and R$_3$ is methyl or benzyl.

39. A process according to claim 38 wherein the compound of formula III prepared is one where R$_2$ is C$_{15}$–C$_{18}$ alkyl and R$_3$ is methyl.

40. A process according to claim 39 wherein the compound of formula III prepared has the formula

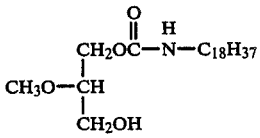

41. A process according to claim 36 wherein X in the compound of formula IV is chloride or bromide.

42. A process according to claim 41 wherein X in the compound of formula IV is bromide.

43. A process according to claim 36 wherein M in the compound of formula V is potassium or sodium.

44. A process according to claim 43 wherein M in the compound of formula V is potassium.

45. A process according to claim 36 wherein the phase transfer catalyst is selected from the group consisting of tetrabutyl ammonium bromide, benzyl triethyl ammonium bromide, methyl triphenyl phosphonium bromide and crown ethers.

46. A process according to claim 45 wherein the phase transfer catalyst is tetrabutyl ammonium bromide.

47. A process according to claim 36 wherein the phase transfer catalyst is present in an amount of from 0.10 to about 0.20 molar equivalents of the diol compound of formula III'.

48. A process according to claim 36 wherein the solvent employed is a lower alkyl (C$_1$–C$_3$) nitrile.

49. A process according to claim 48 wherein the solvent employed is acetonitrile.

50. A process according to claim 36 wherein the temperature is from 20° to 100° C.

51. A process according to claim 50 wherein the temperature is from 25° to 100° C.

52. A process according to claim 36 for preparing a compound of formula III:

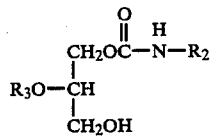

where
R$_2$ is C$_{15}$–C$_{18}$ alkyl; and
R$_3$ is methyl,
which comprises reacting a diol compound of formula III':

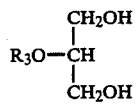

where
R$_3$ is as defined above,
with an organic halide of formula IV:

D—X                                                          IV where
D has the same significance as that defined above for R$_2$; and
X is halide,
and an alkali metal cyanate of formula V:

M—OCN where
M is an alkali metal, in the conjoint presence of a phase transfer catalyst selected from the group consisting of tetrabutyl ammonium bromide, benzyl triethyl ammonium bromide, methyl triphenyl phosphonium bromide and 18-crown-6 and a lower alkyl (C$_1$–C$_3$)nitrile at a temperature of from 25° to 100° C. to obtain said compound of formula III, the phase transfer catalyst being present in an amount of from 0.10 to about 0.20 molar equivalents of the diol compound of formula III'.

* * * * *